United States Patent [19]

Kawano

[11] Patent Number: 5,733,245

[45] Date of Patent: Mar. 31, 1998

[54] ENDOSCOPE PROVIDED WITH CURVED PORTION PROTECTING MECHANISM

[75] Inventor: Hirotaka Kawano, Omiya, Japan

[73] Assignee: Fuji Photo Optical Co., Ltd., Omiya, Japan

[21] Appl. No.: 763,147

[22] Filed: Dec. 10, 1996

[30] Foreign Application Priority Data

Dec. 19, 1995 [JP] Japan .................. 7-348678

[51] Int. Cl.$^6$ .................................................. A61B 1/00
[52] U.S. Cl. .................. 600/144; 600/139; 600/146
[58] Field of Search .................. 600/144, 139, 600/140, 141, 146, 149, 150, 153, 104, 106, 114

[56] References Cited

U.S. PATENT DOCUMENTS

| | | | |
|---|---|---|---|
| 3,854,473 | 12/1974 | Matsuo | 600/144 X |
| 4,374,525 | 2/1983 | Baba | 600/146 X |
| 4,807,593 | 2/1989 | Ito | 600/114 |
| 4,928,669 | 5/1990 | Sullivan | 600/144 |
| 4,971,033 | 11/1990 | Ehlers | 600/144 X |
| 5,025,778 | 6/1991 | Silverstein et al. | 600/144 X |
| 5,168,864 | 12/1992 | Shockey | 600/144 |
| 5,179,935 | 1/1993 | Miyagi | 600/144 X |
| 5,197,457 | 3/1993 | Adair | 600/144 X |
| 5,251,611 | 10/1993 | Zehel et al. | 600/144 X |
| 5,531,687 | 7/1996 | Snoke et al. | 600/146 X |

Primary Examiner—Beverly M. Flanagan
Attorney, Agent, or Firm—Ronald R. Snider

[57] ABSTRACT

An endoscope provided with a curved portion protecting mechanism which is capable of straightening the curved portion securely and protecting the insertion portion itself from damage. The endoscope is provided with an end portion [ac] in which an observing means is disposed and an insertion portion including a curved portion which is freely bent, the insertion portion being inserted into a body cavity through a mantle tube. A flexible tube is laid from the end portion to a predetermined position through the curved portion, and a hard straightening rod for straightening the curved portion is withdrawably disposed in the flexible tube. A rack-and-pinion mechanism is connected to the straightening rod, which is advanced and withdrawn by a rotary operating means of an endoscope operating portion. In this manner, when the straightening rod is inserted into the flexible tube by the rotary operating means, the curved portion is straightened securely.

3 Claims, 4 Drawing Sheets

ENDOSCOPE PROVIDED WITH CURVED PORTION PROTECTING MECHANISM

BACKGROUND OF THE INVENTION

This application claims the priority of Japanese Patent Application No. 7-348678 filed on Dec. 19, 1995 which is incorporated herein by reference.

1. Field of the Invention

The present invention relates to a structure of an endoscope provided with a curved portion protecting mechanism and more particularly, to a structure of a curved portion protecting mechanism which is applicable to an endoscope the insertion portion of which is introduced to a body cavity through a mantle tube.

2. Description of the Related Art

Endosocopes (including electronic endoscopes) have conventionally been used as intraperitoneal mirrors. Such endoscopes are provided with an end portion, an insertion portion composed of a curved portion and a hard portion, and an operating portion at the rear end portion of the insertion portion. The insertion portion of the endoscope is inserted into a body cavity through a mantle tube.

FIG. 6 shows an endoscope in use as an intraperitoneal mirror. At the time of treatment, a mantle tube 1 is first inserted into an abdominal cavity, and an endoscope 2 is then inserted thereinto through an internal cylinder of the mantle tube 1, as shown in FIG. 6. An objective optical system for observing an internal structure is disposed at the end portion 3 of the endoscope 2, and the end portion 3 is connected to a curved portion 4. Consequently, it is possible to freely bend the end portion 3 by operating the curved portion 4 with an angle control knob (not shown) so as to dispose the end portion 3 at a desired position while the internal structure is being observed through the objective optical system. Thereafter, a manipulating tool is introduced through a manipulating tool insertion channel within the endoscope 2 for surgical treatment such as extirpation of a gall bladder.

According to the above-described structure of the endoscope 2, however, when the endoscope 2 is extracted from the mantle tube 1 after treatment, if the curved portion 4 remains bent, it breaks the cover of the curved portion 4 or the end portion, which may impair the airtightness or greatly damages an angling ring or the like within the curved portion 4. In other words, since the end of the mantle tube 1 is processed so as to have a sharp edge which facilitates insertion into an abdomen cave, if the curved portion 4 remains bent even to a slight extent, it is damaged when it is pulled through the mantle tube 1.

It is therefore necessary in an endoscope having such a curved portion 4 to straighten the curved portion 4 with the angle control knob of the operating portion and confirm the straightened state when the endoscope is extracted.

However, it is often the case that the curved portion 4 is not straightened enough in spite of the straightening operation or the angle control knob is carelessly touched in the course of extraction, which bends the curved portion 4 against the will. That is, these problems cannot be solved completely only by the operation of the angle control knob.

SUMMARY OF THE INVENTION

Accordingly, it is an object of the present invention to eliminate the above-described problems in the related art and to provide an endoscope provided with a curved portion protecting mechanism which is capable of straightening the curved portion securely and which does not damage the insertion portion itself.

To achieve this end, an endoscope provided with a curved portion protecting mechanism according to the present invention comprises: an end portion at which an observing means is disposed; an insertion portion including a curved portion which is connected to the end portion in such a manner as to be freely bent, the insertion portion being inserted into a body cavity through a mantle tube; a flexible tube laid from the end portion to a predetermined position through the curved portion; and a hard straightening rod for straightening the curved portion which is disposed in the flexible tube in such a manner as to be freely advanced and withdrawn at least in the flexible tube within the curved portion.

The endoscope may further comprise a rotary operating portion disposed at an endoscope operating portion; and a rack-and-pinion mechanism for converting the rotation of the rotary operating portion into a rectilinear motion which advances or withdraws the straightening rod.

The observing means may be an ultrasonic transducer for obtaining an ultrasonic image. Although an objective optical system is generally disposed as the observing means, an ultrasonic transducer may be provided in place of or together with the objective optical system.

According to the above-described structure, it is possible to straighten the curved portion and keep its state by inserting the straightening rod into the flexible tube, thereby protecting the insertion portion of the endoscope from damage when it is extracted from the mantle tube.

The above and other objects, features and advantages of the present invention will become clear from the following description of the preferred embodiment thereof, taken in conjunction with the accompanying drawings.

DESCRIPTION OF THE PREFERRED EMBODIMENT

Figure 1:
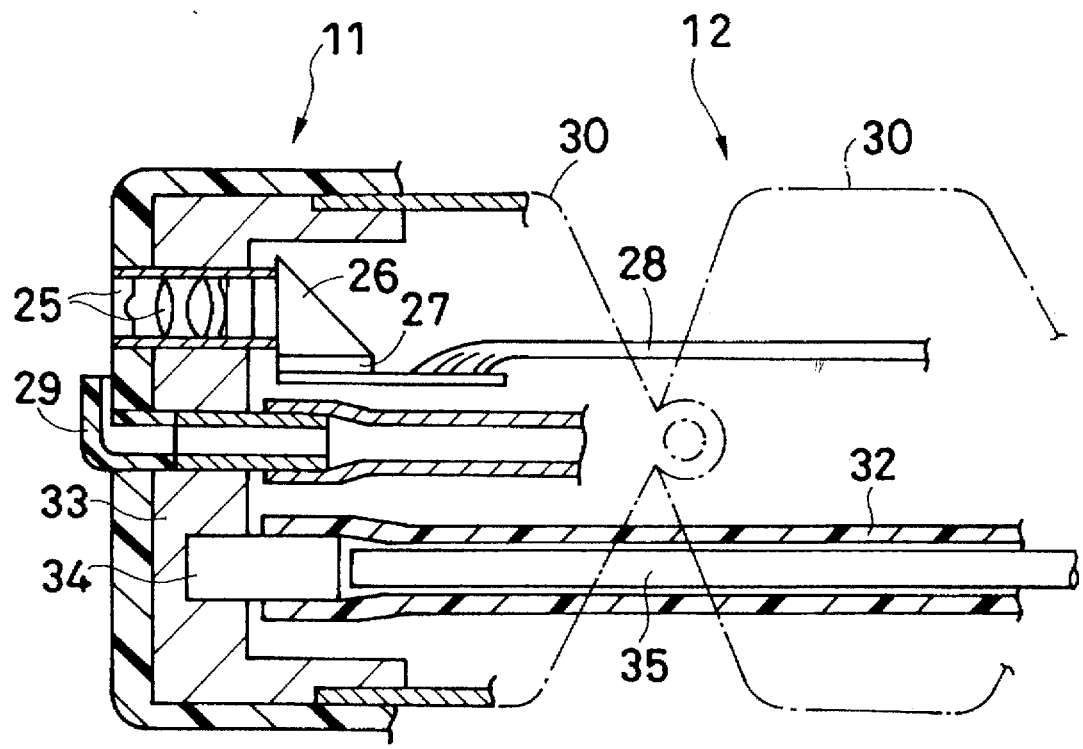
FIG. 1 is a sectional view of the internal structure of the end portion and the curved portion of an embodiment of an endoscope provided with a curved portion protecting mechanism according to the present invention.
Figure 2:
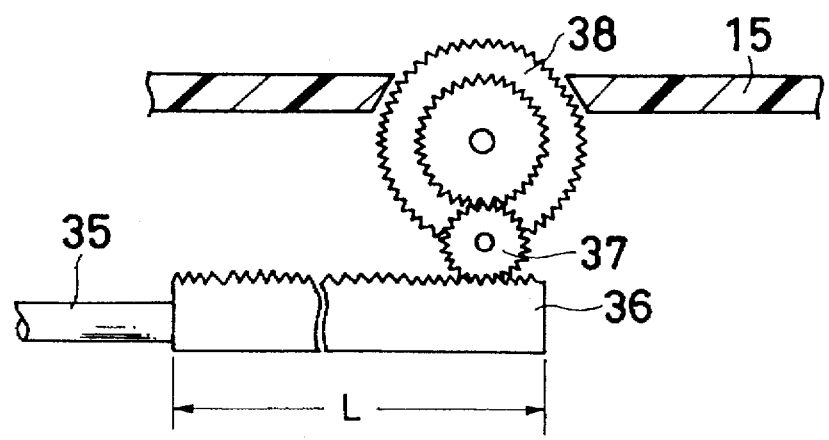
FIG. 2 shows the structure of a straightening rod driving means in the operating portion of the embodiment shown in FIG. 1.
Figure 3:
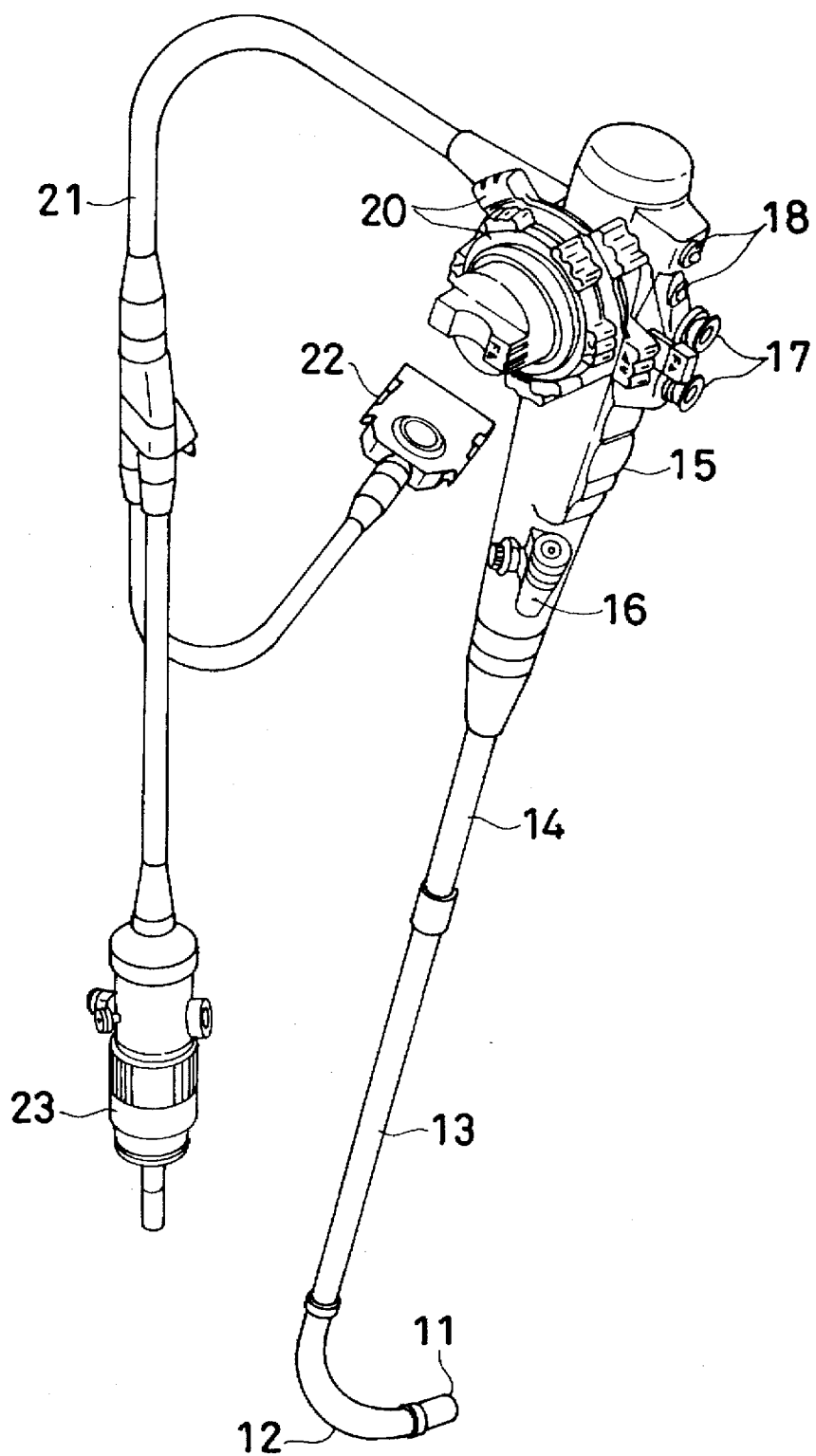
FIG. 3 shows the entire part of the endoscope.
Figure 4:
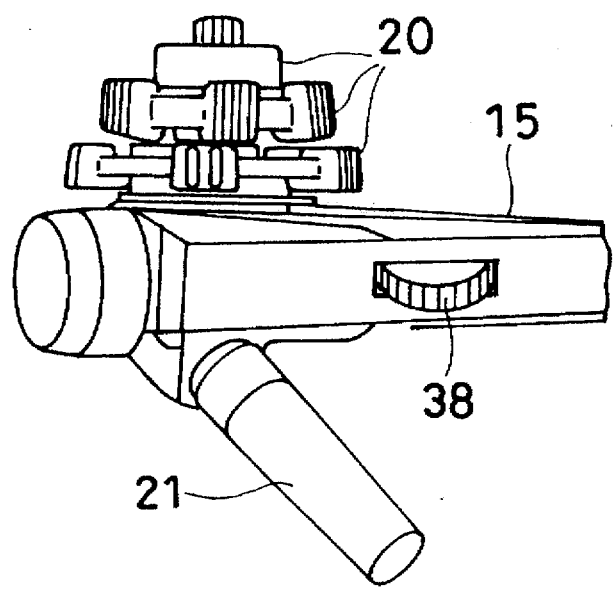
FIG. 4 is an external view of the operating portion of the endoscope.

FIGS. 1 to 4 show the structure of an embodiment of an endoscope provided with a curved portion protecting mechanism according to the present invention, wherein FIG. 1 shows the structure of the end portion of the endoscope, FIG. 2 shows the structure of a driving means of a straightening rod, FIG. 3 shows an entire part of the endoscope and FIG. 4 is an external view of the operating portion. In FIG. 3, the endoscope is composed of an end portion 11, a curved portion 12, a hard portion (insertion portion) 13, an interlocking portion 14, and an operating portion 15. The operating portion 15 is provided with a forceps insertion hole 16 through which a manipulating tool is introduced to the end portion, operating valve members 17 for supplying air and water to the observation window at the end portion 11 and sucking an undesired substance from the end portion 11, an operating switch 18 used at the time of photographing, an angle control knob 20 for bending the curved portion 12, and the like.

A connector 22 for a processor and a connector for a light source are connected to the operating portion 15 through a forked cable 21. This endoscope is an electronic endoscope, and the video signals obtained by an imaging device at the end portion 11 are transmitted to the processor through the connector 22. Light for irradiating a body cavity is supplied to the end portion through the connector 23 and a light guide.

In FIG. 1, an objective optical system 25 is disposed at the end portion 11. A CCD (Charged Coupled Device) 27 is connected to the objective optical system 25 through a prism 26, and the video signals obtained by the CCD 27 are transmitted to the processor through a signal line 28. An air and water supply nozzle 29 is disposed in the vicinity of the objective optical system 25, and air and water are jetted onto the observation window at the endmost portion of the objective optical system 25 therethrough by means of the operation valve members 17. The light guide for supplying irradiation light is also provided at the end portion 11.

In the curved portion 12 provided at the back of the end portion 11, a plurality of angling rings 30 are connected each other such that the portions which are in contact with the inner wall of the curved portion 12 are shorter than the central portions. These angling rings enable the curved portion 12 to be bent vertically and horizontally. A wire (not shown) connecting the end portion 11 and the angle control knob 20 of the operating portion 15 is provided therebetween, and by driving the wire with the angle control knob 20, the curved portion 12 is bent.

A flexible guide tube 32 is disposed at the end portion 11 and the curved portion 12. The guide tube 32, which is composed of a tube of, for example, a synthetic resin tube incorporating a reticulate member, is secured to a supporting portion 33 at the end portion 11 with a fixing member 34 and it is extended up to the operating portion 15. A straightening rod 35 which can be freely advanced and withdrawn in the flexible guide pipe 32 is provided therein. The straightening rod 35 is a hard rod made of, for example, stainless steel. The straightening rod 35 is so positioned as to be withdrawn into the hard portion 13 when it is not used, and introduced into the curved portion 12 when it is used.

As shown in FIG. 2, the straightening rod 35 is connected to a rack member 36 having a length L which is equivalent to the length of the curved portion 12. The rack member 36 meshes a pinion 37, and a rotary operating portion 38 is provided in the operating portion 14 in such a manner as to mesh the pinion 37. The rotary operating portion 38 protrudes from the outer wall of the operating portion 15. As shown in FIG. 4, the rotary operating portion 38 is disposed on the opposite side of the operation valve members 17, for example.

Figures 5A, 5B:
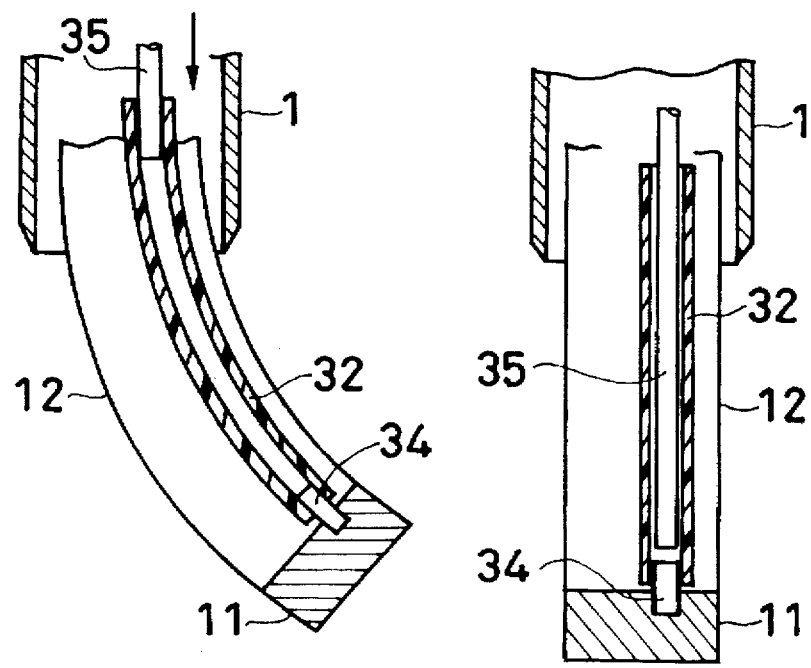
FIG. 5(A) is a sectional view of the embodiment shown in FIG. 1 before the insertion of a straightening rod.
FIG. 5(B) is a sectional view of the embodiment shown in FIG. 1 after the insertion of a straightening rod.
Figure 6:
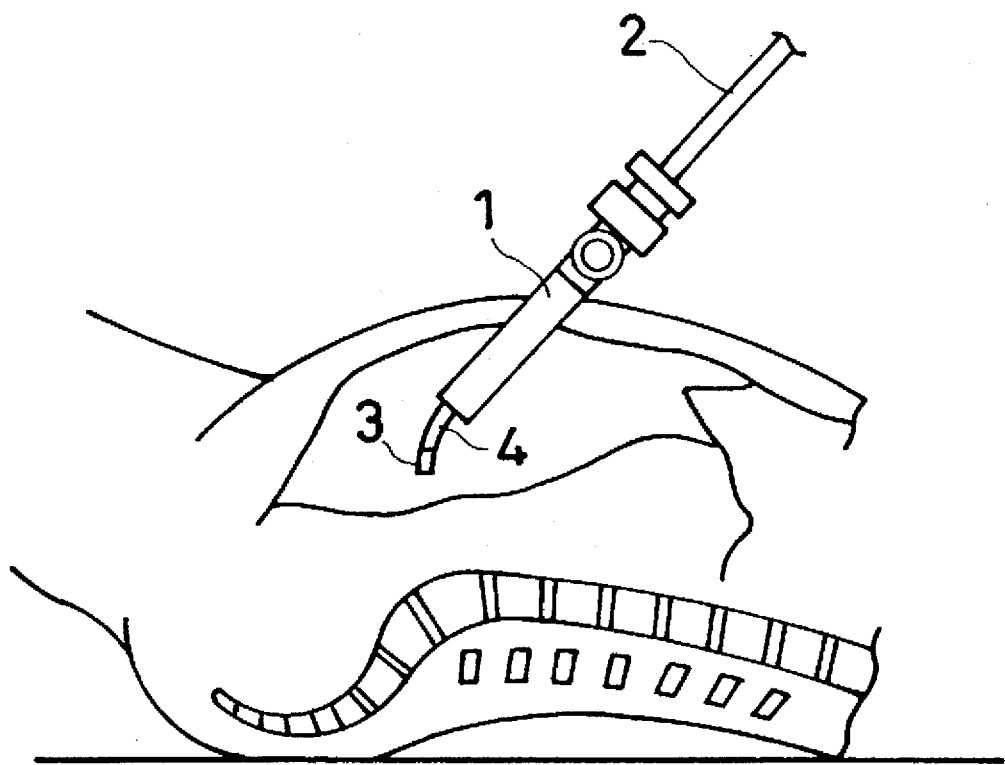
FIG. 6 is an explanatory view of an endoscope which is in use as an intraperitoneal mirror.

The operation of the embodiment of an endoscope having the above-described structure will now be explained with reference to FIGS. 5(A) and 5(B). When this endoscope is used as an intraperitoneal mirror, a mantle tube 1 is first inserted into an abdominal cavity, as explained in FIG. 6, and then the insertion portion (11, 12, 13) is inserted into the abdominal cavity with a mantle tube 1 as a guide. After the end portion 11 is faced toward the diseased part by bending the curved portion 12, a manipulating tool is introduced from the forceps insertion hole 16 shown in FIG. 3 through a manipulating tool insertion channel, and predetermined treatment is executed while the diseased part is being observed.

After such treatment is finished and while the curved portion 12 assumes a neutral state, for example, if the rotary operating portion 38 of the operating portion shown in FIG. 2 is rotated, the straightening rod 35 is pushed from the hard portion 13 toward the forward end by means of the rack 36 and the pinion 37. Then the straightening rod 35 passes through the guide tube 32 within the curved portion 12, as shown in FIG. 5(A) while straightening the curved portion 12, as shown in FIG. 5(B). Since the insertion portion of the endoscope is extracted from the mantle tube 1 after this operation, neither the cover of the curved portion 12 or the end portion 11 nor the interior members are damaged. By reversely rotating the rotary operating portion 38 after the end of extraction, the straightening rod 35 is withdrawn and stored into the hard portion 13.

Although the straightening rod 35 is advanced and withdrawn by the rotary operating portion 38 in this embodiment, it is possible to provide, for example, an insertion hole similar to the forceps insertion hole 16 in the guide tube 32 at an appropriate position of the operating portion and to insert and extract the straightening rod 35 through the insertion hole.

It is also possible to reverse the relationship between the guide tube 32 and the straightening rod 35. In other words, the guide tube 32 may be a flexible linear member, and the straightening rod 35 may be a tubular rod. However, various members such as light guide, signal line, manipulating tool insertion channel and air and water and supply nozzle are disposed within the endoscope. From the point of view of protection of these members, the structure of inserting the straightening rod 35 into the guide tube 32 is preferable.

In addition, although the objective optical system is provided as an observing means in the embodiment, it is possible to dispose an ultrasonic transducer at the end portion instead. That is, it is possible to form an ultrasonic image by transmitting and receiving ultrasonic waves by using the ultrasonic transducer, and processing the received signals in the same way as in an ultrasonic diagnostic apparatus.

As explained above, according to the present invention, it is possible to straighten the curved portion securely when the endoscope is extracted, not by the operation of the angle control knob but by the use of the flexible tube and the hard straightening rod. It is therefore possible to protect the curved portion and the end portion from damage and to prevent the airtightness from being impaired and the interior members of the curved portion from being greatly damaged.

These advantages can also be gained in an endoscope for forming an ultrasonic image.

While there has been described what are at present considered to be a preferred embodiment of the invention, it will be understood that various modifications may be made thereto, and it is intended that the appended claims cover all such modifications as fall within the true spirit and scope of the invention.

What is claimed:

1. An endoscope provided with a curved portion protecting mechanism comprising:
    an end portion at which an observing means is disposed;
    an insertion portion including a curved portion which is connected to said end portion in such a manner as to be freely bent, said insertion portion being inserted into a body cavity through a mantle tube;

a flexible guide tube disposed from said end portion to a predetermined position through said curved portion; and a hard straightening rod for straightening said curved portion which is disposed in said flexible tube in such a manner as to be freely advanced and withdrawn at least in said flexible tube within said curved portion; and wherein said hard straightening rod is pushed forward into said flexible guide tube thereby straightening said curved portion.

2. An endoscope provided with a curved portion protecting mechanism according to claim 1, further comprising:

a rotary operating portion disposed at an endoscope operating portion; and a rack-and-pinion mechanism for converting the rotation of said rotary operating portion into a rectilinear motion which advances or withdraws said straightening rod.

3. An endoscope provided with a curved portion protecting mechanism according to claim 1, wherein said observing means is an ultrasonic transducer for obtaining an ultrasonic image.

* * * * *